United States Patent [19]

Pittet et al.

[11] 3,980,708

[45] Sept. 14, 1976

[54] PROCESS FOR PREPARING ALPHA-SUBSTITUTED ACETALDEHYDES

[75] Inventors: Alan Owen Pittet, Atlantic Highlands; Erich Manfred Klaiber, Neptune, both of N.J.

[73] Assignee: International Flavors & Fragrances Inc., New York, N.Y.

[22] Filed: July 8, 1975

[21] Appl. No.: 594,100

Related U.S. Application Data

[63] Continuation-in-part of Ser. No. 507,414, Sept. 19, 1974.

[52] U.S. Cl. .............................................. 260/598
[51] Int. Cl.[2] .............................................. C07C 45/00
[58] Field of Search ............................ 260/598, 599

[56] References Cited

OTHER PUBLICATIONS

Wenkert et al., Nature, vol. 170 (1952) pp. 708–709

*Primary Examiner*—Bernard Helfin
*Attorney, Agent, or Firm*—Arthur L. Liberman; Harold Haidt; Franklin D. Wolffe

[57] ABSTRACT

Process described is for the preparation of 2,2,6-trimethyl-1-cyclohexen-1-ylacetaldehyde having the structure:

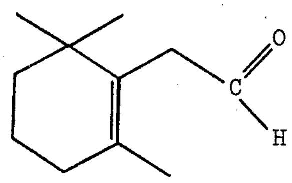

(hereinafter referred to as beta-cyclohomocitral) which comprises the step of oxidizing beta-ionone with hydrogen peroxide in the presence of inorganic base to form beta-cyclo-homocitral, directly.

4 Claims, No Drawings

PROCESS FOR PREPARING ALPHA-SUBSTITUTED ACETALDEHYDES

This application is a continuation-in-part of copending application for U.S. Pat. Ser. No. 507,414 filed Sept. 19, 1974.

BACKGROUND OF THE INVENTION

Beta-cyclohomocitral is a valuable substance useful in the formulation of perfumery, tobacco and food flavoring materials, as disclosed in copending application for U.S. Pat. No. 507,412 filed on Sept. 19, 1974.

The preparation of beta-cyclohomocitral and beta-ionone enol acetate (an intermediate for producing beta-cyclohomocitral is set forth in British Pat. No. 775,060, which discloses (A) first forming an iso-$C_{11}$-aldehyde by (i) condensing ethoxy-acetylene with 2,6,6-trimethylcyclohexanone-1, (ii) partially hydrogenating the resulting acetylenic carbinol so as to convert the triple bond therein into a double bond, and (iii) treating the resulting olefinic compound with an acid; then (B) reacting the resulting iso-$C_{11}$-aldehyde with acetic anhydride and fused sodium acetate under reflux conditions to form beta-ionone enol acetate; and (C) hydrolyzing the beta-ionone enol acetate with alcoholic base (sodium bicarbonate-methanol mixture) to form beta-cyclohomocitral. This multi-step sequence of reactions and the low yield of final product render the synthesis of British Pat. No. 775,060 commercially impractical.

Reactions of peracetic acid with α-aralkylidenecyclanones in the presence of buffer are disclosed by Walton J. Org. Chem., 22, 1161 (1957), for example:

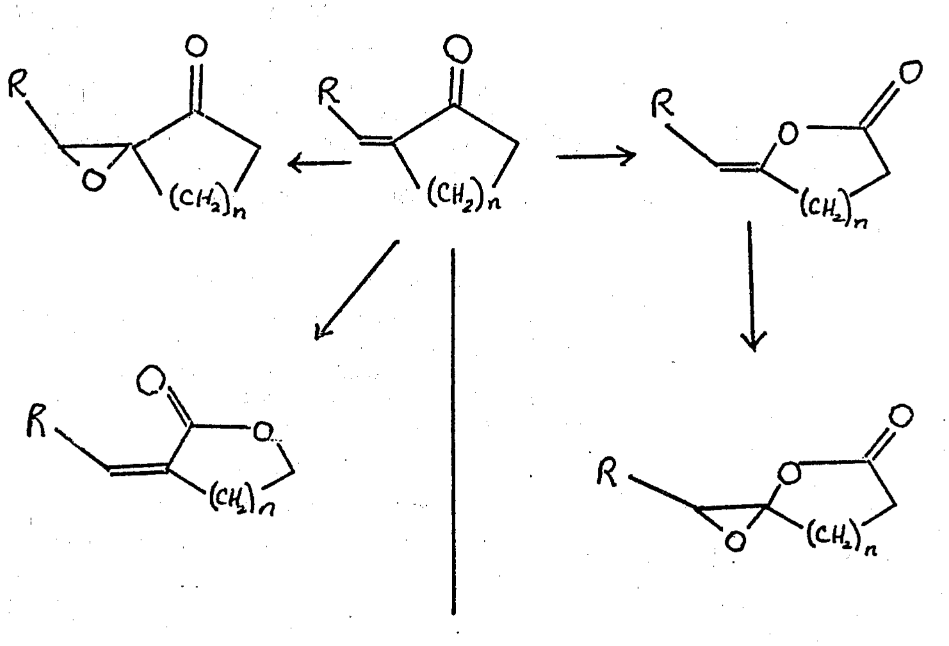

wherein R is phenyl, substituted phenyl or 2-furyl and $n$ is 3 or 4.

Broadly, the reaction of a system containing conjugated unsaturation with a peroxidation agent is known (See Wenkert and Rubin, Nature 170, 708 (1952) wherein the reaction of an alpha, beta-unsaturated ketone having a phenyl moiety in the beta position is oxidized to form an enol ester is taught) but reaction of an ionone type material with an oxidizing agent to form an acyloxyethylene moiety (as opposed to an epoxide moiety) has been heretofore unknown. Also see Boesken et al., Rec. Trav. Chim. 50, 827 (1931); 52, 874 (1933); 55, 786 (1936), who have shown that peroxyacetic acid reacts with benzalacetone and related ketones with the insertion of an oxygen atom between the carbonyl and styryl groups, resulting in the formation of enol esters of phenylacetaldehyde and benzyl ketones. A relevant reaction taught by Boesecken et al. is as follows:

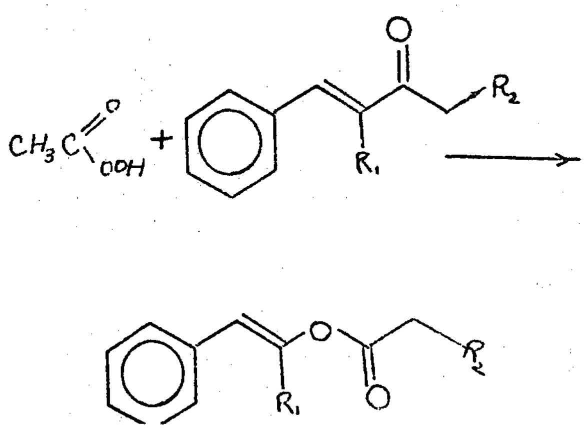

wherein $R_1$ and $R_2$ are each hydrogen or methyl.

FMC Corporation "Preparation, Properties, Reactions and Uses of Organic Peracids and Their Salts" discloses methods for the preparation of peracetic acid, performic acid and perpropionic acid at pages 3–21 and discusses the use of peracids in carrying out Baeyer-Villiger oxidations of unsaturated ketones at pages 84–89.

The invention accordingly comprises the novel process and steps, specific embodiments of which are also described hereinafter by use of experiments and in accordance with what is now the preferred practice of the invention.

Briefly, the process of this invention comprises forming beta-cyclohomocitral by oxidizing beta-ionone with hydrogen peroxide in the presence of inorganic base in one step.

The strength of hydrogen peroxide used is from about 10 percent up to about 50 percent; preferably, 30 percent aqueous hydrogen peroxide. The inorganic base used may be an alkali metal hydroxide or alkali metal carbonate such as sodium carbonate, potassium carbonate, lithium carbonate, sodium hydroxide, potassium hydroxide or lithium hydroxide; preferably sodium hydroxide. The mole ratio of hydrogen peroxide:beta-ionone is preferably from about 1.1:1 up to about 3:1.

The process of our invention is specific to beta-ionone. As further exemplified infra, when the reaction conditions of our process are applied to alpha-ionone, as opposed to beta-ionone, epoxide formation occurs and no beta-cyclohomocitral is formed.

Example I serves to illustrate our invention as it is now preferred to practice it. Example VI following, serves to illustrate the unworkability of the process of our invention where dimethyl formamide is used in the oxidation reaction of beta-ionone with peracetic acid. Examples II-V illustrate the utility of beta-cyclohomocitral, the product of the process of our invention. It will be understood that these examples are illustrative and the invention is to be considered restricted thereto only as indicated in the appended claims.

EXAMPLE I

Preparation of beta-cyclohomocitral by $H_2O_2$ peroxidation of beta-ionone

To 20 grams of beta-ionone in 100 ml methanol is added 12 ml of 30% hydrogen peroxide. The solution is then cooled to 15°C and 18 ml 6 molar aqueous sodium hydroxide is added over a period of 30 minutes while maintaining the reaction mixture at 15°C. The reaction mixture is then allowed to warm up to 30°C and then maintained at 30°C with external cooling. The exotherm lasts approximately 60 minutes. Examination of the reaction product by gas chromatography indicates that some beta-ionone is still present. An additional 12 ml of 30% $H_2O_2$ and 18 ml 6 molar aqueous NaOH are added during a 30-minute period while maintaining the temperature at 25°C. Again an exotherm occurs lasting approximately 60 minutes during which time the temperature is maintained at 30°C. The reaction mass is then poured into excess water (500 ml) and the product is then extracted with three 150 ml portions of diethyl ether. The combined ether extracts are then washed with two 150 ml portions of saturated sodium chloride solution and dried over anhydrous $MgSO_4$. The solvent is then evaporated to yield 16.8 grams of a crude oil.

Examination of this material by gas chromatography indicates 22% beta-cyclohomocitral.

The desired product is obtained by preparative gas chromatography (conditions: 10′ × 1/4″ 10% carbowax 20 M packed stainless steel column at 220°C isothermal).

The structure is confirmed by IR, MS and NMR analyses as being:

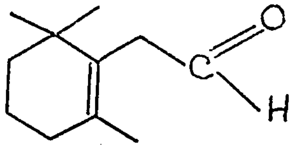

EXAMPLE II

Petitgrain Formulation

The following mixture is prepared:

| Ingredients | Parts by Weight |
|---|---|
| Betacyclohomocitral (produced according to the process of Example I) | 20 |
| Linalool | 500 |
| Linalyl Acetate | 600 |
| Dimethyl Anthranilate | 2 |
| Terpineol | 20 |
| Geraniol | 30 |
| Terpinyl Acetate | 10 |
| Geranyl Acetate | 5 |
| Ocimene | 20 |
| Limonene | 50 |
| Pinene | 20 |
| Nerolidol | 10 |

The beta-cyclohomocitral imparts the green, earthy note of petitgrain required in such petitgrain formulations.

EXAMPLE III

Preparation of a soap composition

100 Grams of soap chips are mixed with one gram of the perfume composition of Example II until a substantially homogeneous composition is obtained. The perfumed soap composition manifests an excellent petitgrain character with excellent green, earthy notes.

EXAMPLE IV

Preparation of a detergent composition

A total of 100 grams of detergent powder is mixed with 0.15 grams of the perfume composition of Example II, until a substantially homogeneous composition is obtained. This composition has an excellent petitgrain aroma with earthy green notes.

EXAMPLE V

Raspberry flavor formulation

The following basic raspberry flavor formulation is produced:

| Ingredients | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl Butyrate | 6.0 |
| Ethyl Acetate | 16.0 |
| Dimethyl Sulfide | 1.0 |
| Isobutyl Acetate | 13.0 |
| Acetic Acid | 10.0 |
| Acetaldehyde | 10.0 |
| Propylene Glycol | 930.0 |

Beta-cyclohomocitral (produced according to the process of Example I) is added to half of the above formulation at the rate of 0.2%. The formulation with the beta-cyclohomocitral is compared with the formulation without the beta-cyclohomocitral at the rate of 0.01 percent (100 ppm) in water and evaluated by a bench panel.

The flavor containing the beta-cyclohomocitral is found to have a substantially more pleasant and better raspberry aroma. It is the unanimous opinion of the bench panel that the chemical, beta-cyclohomocitral rounds the flavor out and contributes to a very natural fresh aroma and taste as found in full ripe raspberries. Accordingly, the flavor with the addition of the beta-cyclohomocitral is considered as substantially better than the flavor without beta-cyclohomocitral.

EXAMPLE VI

Formation of alpha-ionone epoxide from alpha-ionone

To 20 grams of alpha-ionone in 100 ml methanol is added 12 ml of 30% hydrogen peroxide. The solution is then cooled to 15°C and 18 ml 6 molar aqueous sodium hydroxide is added over a period of 30 minutes while maintaining the reaction mixture at 15°C. The reaction mixture is then allowed to warm up to 30°C and then maintained at 30°C with external cooling. The exotherm lasts approximately 60 minutes. Examination of the reaction product by gas chromatography indicates that some alpha-ionone is still present. An additional 12 ml of 30% $H_2O_2$ and 18 ml 6 molar aqueous NaOH are added during a 30 minute period while maintaining the temperature at 25°C. Again an exotherm occurs lasting approximately 60 minutes during which time the temperature is maintained at 30°C.

The reaction mass is then poured into 500 ml water and the product is extracted with three 150 cc portions of diethyl ether. The ether extracts are combined and washed with two 100 cc portions of saturated sodium chloride solution and dried over anhydrous magnesium sulfate. The residual oil obtained after stripping the solvent, is distilled at 93°–99°C at 0.5 mm Hg pressure yielding 28.3 g of a clean colorless liquid.

IR, MS and NMR analyses comfirm the fact that the product is alpha-ionone epoxide having the structure:

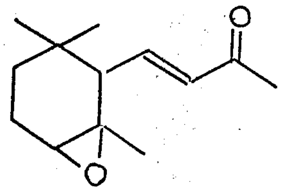

What is claimed is:

1. A process for preparing 2,2,6-trimethyl-1-cyclohexen-1-ylacetaldehyde consisting essentially of the step of intimately admixing hydrogen peroxide, an inorganic base and beta-ionone, said hydrogen peroxide being in the form of from 10 up to 50% aqueous hydrogen peroxide; said inorganic base being selected from the group consisting of alkali metal hydroxides and alkali metal carbonates; and the mole ratio of hydrogen peroxide:beta ionone being from about 1.1:1 up to about 3:1.

2. The process of claim 1 wherein the hydrogen peroxide is in the form of 30% aqueous hydrogen peroxide.

3. The process of claim 1 wherein the inorganic base is aqueous sodium hydroxide.

4. The process of claim 1 wherein the reaction is carried out in the presence of methyl alcohol.

* * * * *

UNITED STATES PATENT AND TRADEMARK OFFICE

CERTIFICATE OF CORRECTION

PATENT NO. : 3,980,708

DATED : September 14, 1976

INVENTOR(S) : Alan Owen Pittet and Erich Manfred Klaiber

It is certified that error appears in the above-identified patent and that said Letters Patent are hereby corrected as shown below:

Column 3, lines 32 and 33: replace, "our invention where dimethyl formamide is used in the oxidation reaction of beta-ionone with peracetic acid." with --- our invention where alpha-ionone is used in the oxidation reaction with peracetic acid. ---

Signed and Sealed this

Fifteenth Day of February 1977

[SEAL]

*Attest:*

RUTH C. MASON
*Attesting Officer*

C. MARSHALL DANN
*Commissioner of Patents and Trademarks*